United States Patent [19]
Kung et al.

[11] Patent Number: 5,643,172
[45] Date of Patent: Jul. 1, 1997

[54] TUBULAR CIRCULATORY ASSIST DEVICE

[75] Inventors: Robert T. V. Kung, Andover, Mass.; Gerard Champsaur, Lyons, France

[73] Assignee: Abiomed R & D, Inc., Danvers, Mass.

[21] Appl. No.: 398,900

[22] Filed: Mar. 6, 1995

[51] Int. Cl.$^6$ ................................................. A61M 1/12
[52] U.S. Cl. ................................................. 600/16
[58] Field of Search ........................... 600/16, 17

[56] References Cited

U.S. PATENT DOCUMENTS

| | | | |
|---|---|---|---|
| 4,014,318 | 3/1977 | Dockum et al. | 600/16 |
| 4,553,532 | 11/1985 | Bohls. | |
| 5,372,573 | 12/1994 | Habib | 600/16 |

OTHER PUBLICATIONS

Liotta D, Manes J, Bourland H, Rodwell D, Hall CW, DeBakey ME, "Recent Modifications in the Implanatable Left Ventricular Bypass." Trans. Amer. Soc. Artif. Int. Organs, 1965; XI: 284–288.

Klain M, Ogawa H, Wright J, Webb J, Mrava G, Von Bally K, Urbanek K, Carse C, Sagawa K, Nose Y, "Valveless Orthotopic Cardiac Prosetheses—A Wave–pulsating Total Heart." Trans. Amer. Soc. Artif. Internal Organs, 1970, XVI:400–408.

Engelman RM, Nyialas E, Lackner H, Godwin SJ, "Left Heart Bypass Without Anticoagulation," J. Thorac. Cardiovasc. Surg. 1971; 62:851–858.

Kung, R.T.V. and G.L. Champsaur (Apr. 1993) "Tubular Pediatric Ventricular Assist Device (VAD)" *ASAIO*, p. 31.

Primary Examiner—William E. Kamm
Attorney, Agent, or Firm—Lahive & Cockfield, LLP

[57] ABSTRACT

A circulatory apparatus for assisting the movement of fluids with a pulsatile flow. The circulatory apparatus includes a restrictable tube, an element for passively restricting a segment of the tube, two or more elements for selectively restricting segments of the tube, and a controller for directing selective restricting elements. The controller directs restricting elements in a manner that provides a cyclical pulsatile pattern of restriction along the length of the tube.

9 Claims, 3 Drawing Sheets

TUBULAR CIRCULATORY ASSIST DEVICE

BACKGROUND OF THE INVENTION

This invention relates to circulatory support devices. More particularly the invention relates to pulsatile circulatory support devices for use in pediatric patients.

The need exists for the use of a circulatory assist device in children and small infants critically ill with heart failure and unresponsive to maximal pharmacologic support. This clinical problem is common in patients following surgery for the correction of congenital heart defects and in patients suffering from acute myocarditis. In both cases, circulatory support aids in the patient's recovery. In patients suffering from irreversible heart failure, a circulatory assist device can act as a bridge to transplantation. A support device can provide for a means of keeping the pediatric patient alive while an acceptable heart donation is found. A device with the abilities to support a patient with terminal heart failure, while awaiting a donor's heart, is highly beneficial in order to maintain an overall organ perfusion and patient well-being thus improving the chance of transplant success.

Currently, centrifugal pumps or extracorporeal membrane oxygenation (hereinafter "ECMO") provide temporary circulatory support for pediatric patients. These methods of providing circulatory support for children have an operative mortality rate in the range of 5 to 25%, depending on the severity of the lesion, the age of the patient, and the expertise of the involved medico-surgical team. The use of centrifugal pumps and ECMO are limited by the higher complication rates caused by these systems. For example, these devices require: a large priming volume resulting in hemodilution; large surface areas leading to hypothermia and to activation of the complement system; high activated clotting time (hereinafter "ACT") levels causing bleeding complications; significant anticoagulants, that in turn cause subsequent bleeding complications; and these devices fail to supply a pulsatile flow. Moreover, these systems require a dedicated technician during the pump run, which may last for several days.

When using ECMO, the priming volume of the whole circuit represents up to three times the patient's blood volume. Although a centrifugal pump requires less priming volume, about 150 cc for the Biomedicus BP 50 "pediatric" head plus tubings, this is nearly one-half the blood volume of a newborn infant. The resulting dilution contributes to coagulation deficiencies and deleterious edematous effects on renal and cerebral functions. In addition, because infants up to six months of age have a poor thermoregulation system, lengthy tubing used in ECMO can promote heat loss leading to hypothermia and impaired coagulation mechanisms.

During ECMO use, the usual recommended level of anticoagulation is such that ACT is kept between 150 to over 200 seconds, depending on the particular system in use. In post-cardiotomy infants, often operated on under deep hypothermia, both dilutional thrombocytopenia and hypothermia induced platelet functional disorders are prominent. In addition, poor hepatic reserve and transient hepatic dysfunction from bypass reduce the production of clotting factors. During ECMO use, high ACT levels may lead to a high probability of bleeding complications, either mediastinal or cerebral.

It is believed that the failure to provide a pulsatile flow results in the high incidence of renal dysfunction during ECMO followed by recovery after the return to pulsatile flow. Moreover, a study in lambs by Champsaur et al., *Pulsatility Improves Hemodynamics During Fetal Bypass*, AHA, 66th Scientific Session, Atlanta, November 1993, paper 1797, p I-335, suggests that even in the short term, pulsatility improves hemodynamics during fetal bypass in which the systemic flow resistance is two times lower under pulsatile as compared to continuous bypass.

Prior pulsatile devices designed for pediatric use have been adaptations of adult devices. In an article by Yu et al., *With and Without a Clamshell*, TransAmerican Society Artificial Internal Organs, 1990, 36: M238-M242, the authors discuss the development of a 20 cc soft ventricular assist device (hereinafter "VAD") while requiring the additional development of a bileaflet valve to improve filling characteristics. Similarly, Taenaka et al., *Experimental Evaluation and Clinical Application of a Pediatric Ventricular Assist Device*, Trans American Society Artificial Internal Organs, 1989, 35: 606–608, has a scaled down 20 cc device using #21 Bjork-Shiley disc valve. The devices of Yu and Taenaka lack simplicity in design and fabrication, and are at the limits of down-sizing due to their valve constraints. Such limitations do not exist for the invention as claimed herein.

Potential applications of the proposed device include the approximately 20,000 pediatric cardiac surgery cases performed in the United States annually. Initial application will be in cases involving post-cardiotomy support subsequent to the correction of congenital heart defect or in patients with cardiopulmonary compromise secondary to myocarditis and/or cardiomyopathy.

SUMMARY OF THE INVENTION

Accordingly, it is an object of the invention to provide a pediatric circulatory support device of improved construction and simpler design that assists movement of liquids or other fluids with a pulsatile flow.

This is accomplished according to a principal aspect of the invention by providing a restrictable tube having a lumen, and by selectively and cyclically restricting the lumen along the length of the tube between an inlet construction and an outlet construction which defines a pumping volume, to provide a pulsatile flow. In a preferred embodiment of the invention, a restricting device controlling the outflow end of the tube adjusts the restricting force applied to the lumen at the outlet based upon the pressure in the lumen extending beyond the tube's outlet. The restricting force applied to the tureen proximal the outlet end of the tube increases, as the pressure in the lumen extending beyond the tube's outlet increases, thereby preventing regurgitation back through the outlet end of the tube. This effectively prevents backflow regardless of the afterload pressure.

BRIEF DESCRIPTION OF THE DRAWINGS

These and other features of the invention will be understood from the following disclosure. In the Drawings.

DETAILED DESCRIPTION OF THE INVENTION

Figure 1:
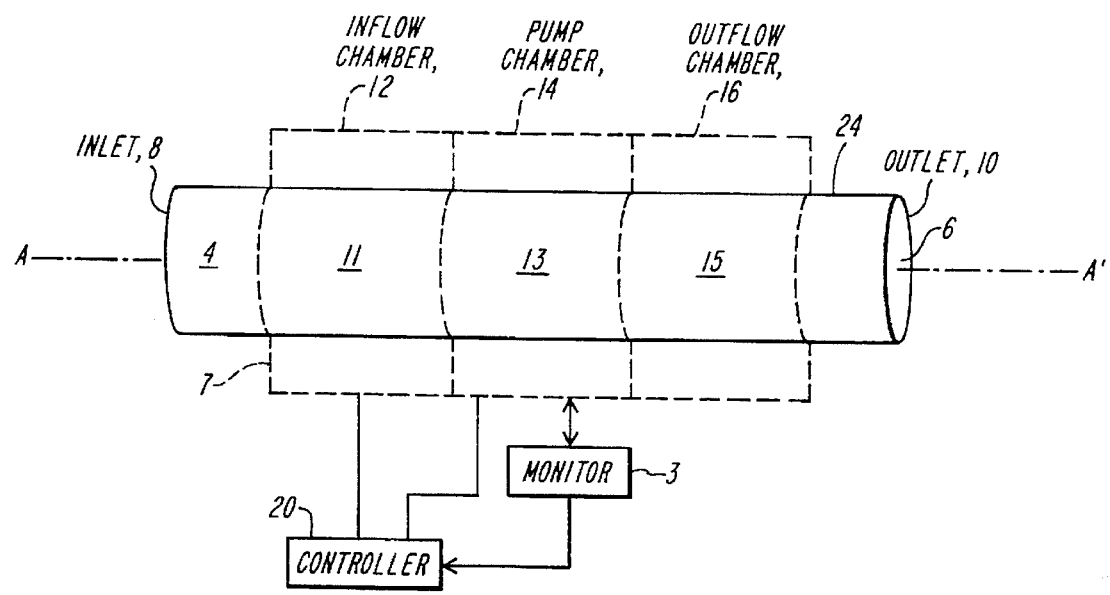
FIG. 1 shows a circulatory assist device according to the present invention.

FIG. 1 illustrates a circulatory assist device 5 according to the invention having a tube 4 elongated along axis A–A', a restricting apparatus 7, and a controller 20. Tube 4 has an outer circumferential surface 9, and an inlet 8 and an outlet 10 connected by a lumen, or passageway, 6. Lumen 6 extends along the direction of axis A–A'.

Restricting apparatus 7 is comprised of three sections or chambers, designated inflow valve chamber 12, pump chamber 14, and outflow valve chamber 16. Preferably, inflow valve chamber 12 is located distal inlet 8, outflow valve chamber 16 is located proximal outlet 10, and pump chamber 14 is located between chambers 12 and 14 along the length of tube 4. Further in accordance with this invention, controller 20 is coupled with inflow chamber 12 and pump chamber 14.

Circulatory assist device 5 may be used, among other things, as a ventricular assist device, or as part of an implantable untethered artificial heart. In either case, circulatory assist device 5 advantageously provides for pulsatile circulatory assistance for pediatric patients, without the inherent medical complications found in prior art devices. In addition, this invention provides for a structure capable of circulating fluids, as gases or liquids with a simple and inexpensive restrictable tubular structure having a passively controlled outlet for preventing regurgitation of any circulated material.

Tube 4 is preferably formed of a flexible and restrictable material. For example tube 4 can be formed of a polyetherurethane, such as ANGIOFLEX™, a material manufactured by ABIOMED, Inc. of Danvers, Mass. The material forming tube 4 is restrictable so that the movement of material flowing through lumen 6 can be controlled. In particular, by restricting tube 4 fluids can be squeezed or pumped along tureen 6, and by further restricting the tube the movement of the fluid can be hindered or completely stopped. In addition, when tube 4 is relaxed or dilated, fluid can be sucked into the newly opened space or cavity formed in lumen 6.

Flow through tube 4 can be selectively controlled by surrounding the outer circumferential surface 9 of tube 4 with a device for restricting one or more particular segments or sections of tube 4. For example, FIG. 1 shows a restricting apparatus 7 surrounding tube 4 and containing three separate restricting chambers: the inflow valve chamber 12, the pump chamber 14, and the outflow valve chamber 16. Inflow chamber 12, pump chamber 14, and outflow chamber 16 can restrict and release, respectively, inflow segment 11, pump segment 13 and outflows segment 15 of tube 4. When a segment of the tube is restricted, a gas or liquid within that segment is forced to move. Alternatively, when a segment of the tube is opened, a vacuum is formed thus causing a gas or liquid to flow in the direction of that particular segment.

Controller 20 actively controls inflow chamber 12 and pump chamber 14. In comparison, outflow chamber 16 is not actively controlled. Rather, outflow chamber 16 provides a passive control.

Controller 20 can electrically, mechanically, hydraulically, or pneumatically actuate inflow chamber 12 and pump chamber 14. In a pneumatically actuating controller, for example, controller 20 applies a variable pressure to inflow chamber 12 and pump chamber 14. The variable pressure may be applied to chambers 12 and 14 via a common driveline with two branches, or via multiple drivelines. When the pressure in the valve chamber 12 rises, the inflow segment 11 of tube 4 surrounded by chamber 12 restricts. Analogously, segment 13 of tube 4 restricts when the pressure in pump chamber 14 rises. When the pressure in chamber 12 or 14 falls, the respective segments surrounded by chamber 12 or 14 dilate. Preferably, inflow chamber 12 and pump chamber 14 are tightly sealed against the outer surface 9 of tube 4, thus preventing any pressure leakage.

Pump systole of circulatory assist device 5 is accomplished by applying phased pressure to both pump chamber 14 and inflow chamber 12, accomplishing unobstructed forward ejection of the active stroke volume. During diastole, vacuum is applied to pump chamber 14 and inflow chamber 12, accomplishing unobstructed and complete filling of pump segment 13. The sequential actuation of the circulatory assist device provides a unidirectional flow similar to the concept of a wave-pulsating blood pump.

Sequential actuation of circulatory assist device 5 can be accomplished by having the ejection from pump segment 13 lag behind the ejection from inflow segment 11, and the filling of pump segment 13 lag behind the filling of inflow segment 11. Thus, the ejection and filling cycle of pump segment 13 and the ejection and filling cycle of segment 11 have the same period, but are phase shifted with each other.

Outflow chamber 16 does not operate under an active controller. Rather, outflow chamber 16 is pressurized to a pre-determined level of static pressure and allowed to remain at that pressure. The pressure in chamber 16 exerts a force on the outflow segment 15 of tube 4 of sufficient magnitude to normally restrict tube 4. Thus, the outflow segment 15 of lumen 6 surrounded by chamber 16 is normally closed.

Outflow segment 15 dilates, or opens, when the material being circulated by circulatory device 5 is forced by pump segment 13 through the restricted opening created by chamber 16 surrounding segment 15 of tube 4. For example, in a pneumatic system, outflow valve segment 15 opens when the level of pressure in pump segment 13 exceeds the level of pressure in chamber 16. Preferably, chamber 16 is pressurized to a level based upon the level of pressure in the circulatory pathway into which circulatory assist device 5 is placed. In particular, chamber 16 is pressurized to a level greater than or equal to the afterload pressure, or the pressure level found in the circulatory pathway connected to outlet 10. Thus, the outflow valve chamber 16 normally restricts outflow in tube segment 15 to a closed position, and chamber 16 allows tube segment 15 to open when the pressure in pump segment 13 exceeds the afterload pressure. By establishing a pressure in outflow chamber 16 higher than the afterload pressure, retrograde flow through tube 4 during diastole is advantageously prevented.

In addition, circulatory assist device 5 can operate over a range of afterload pressures when the pressure for chamber 16 is set at a sufficiently high value and when the drive pressure exerted by pump segment 13 is satisfactory. For example, when the pressure in chamber 16 is set at a level exceeding the afterload pressure, regurgitation through outlet 10 is prevented over a range of afterload pressures. When the pressure exerted by pump chamber 14 on tube segment 13 exceeds the high static pressure level in chamber 16, a fluid being circulated can still be forced through the restriction in tube segment 15.

Figure 2:
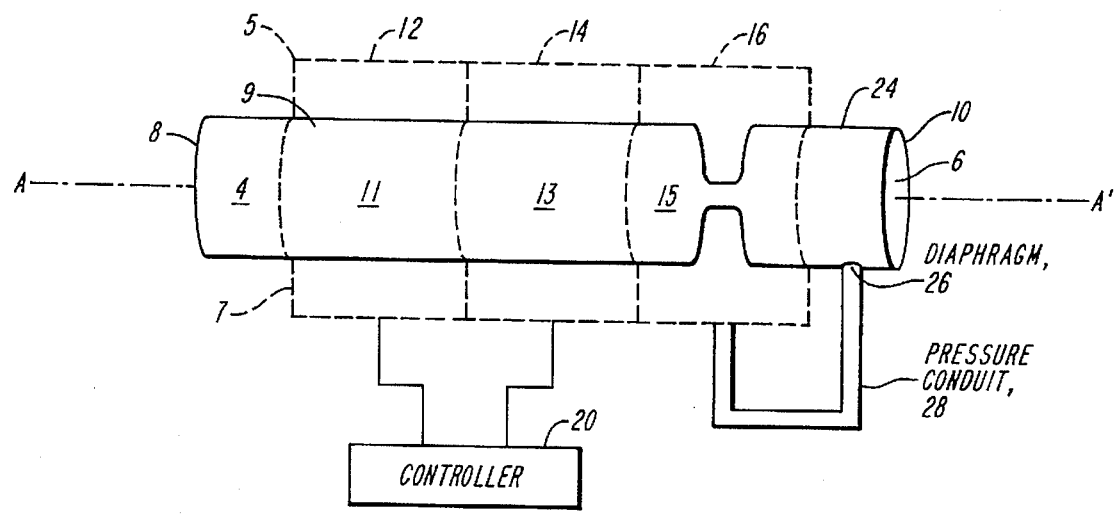
FIG. 2 shows another embodiment of a circulatory assist device according to the present invention.

FIG. 2 illustrates circulatory assist device 5 wherein outflow chamber 16 is referenced to the afterload pressure using a pressure conduit 28 and wherein outflow segment 15 is formed in a normally closed position. In particular, pressure conduit 28 is connected at a first end to outflow chamber 16 and at a second end to a structure pressurized to the afterload pressure, such as an extension 24 of lumen 6. The first end of conduit 28 opens onto the interior of outflow chamber 16, while the second end of conduit 28 contains a diaphragm 26 communicating with the fluid pressure within tube extension 24. Thus, one side of diaphragm 26, generally the concave side, contacts the pressurized fluid contained within chamber 16 and conduit 28, and the other side of diaphragm 26, generally the convex side, is in contact with the fluid being circulated at the extension 24. In addition, tube segment 15 is partially flattened to create a normally closed segment.

This structure allows the fluid being circulated to communicate with the pressurized fluid in outflow chamber 16, thus preventing regurgitation through outlet 10 regardless of the range of afterload pressures. For example, if the afterload pressure exceeds the normal static pressure in chamber 16, the afterload pressure will exert an additional force on diaphragm 26. Diaphragm 26 in turn increases the pressure in chamber 16, thereby reinforcing the restrictive pressure applied to lumen 6 and preventing regurgitation through outlet 10.

This technique works under all afterload pressures without excessively pressurizing chamber 16 or lumen 6. This embodiment also has the additional advantage that in a failure mode (i.e. failure of the pressure controllers) the outflow chamber of lumen 6 is automatically closed, thereby avoiding retrograde flow into circulatory support apparatus 5.

Figure 3:
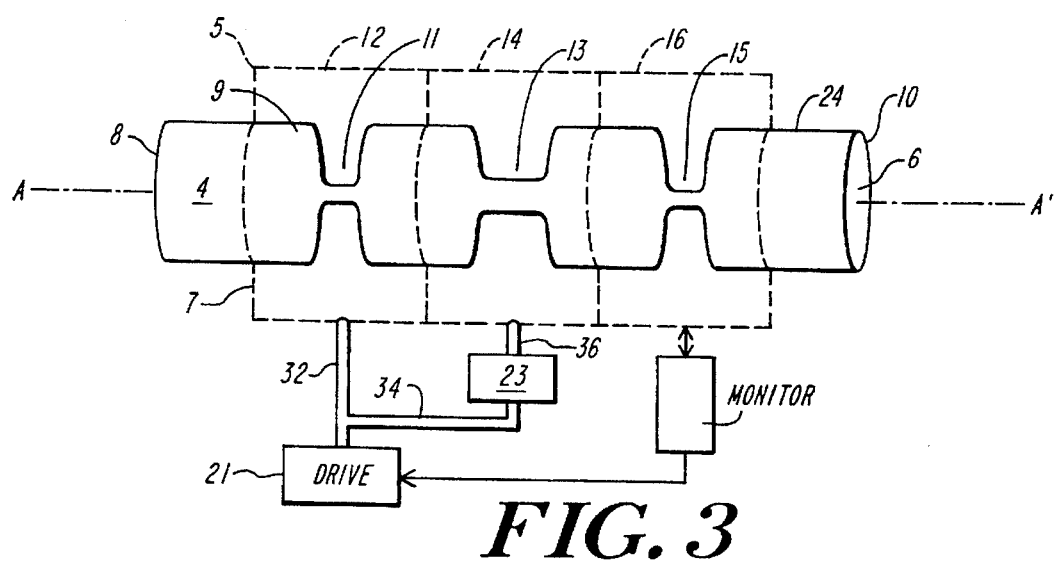
FIG. 3 shows additional features of a circulatory assist device according to the present invention.

FIG. 3 illustrates an embodiment of this invention having a specialized pressure controller. In particular, this invention contemplates a controller having a single pneumatic drive 21 and a flow restrictor 23. In this embodiment, pneumatic lines 32, 34 and 36 connect inflow chamber 12, pneumatic drive 21, flow restrictor 23, and pump chamber 14. FIG. 3 further illustrates an inflow segment 11 of tube 4 surrounded by inflow chamber 12, an outflow segment 15 of tube 4 surrounded by outflow chamber 16, and a pump segment 13 of tube 4 surrounded by pump chamber 14.

Figure 4A:
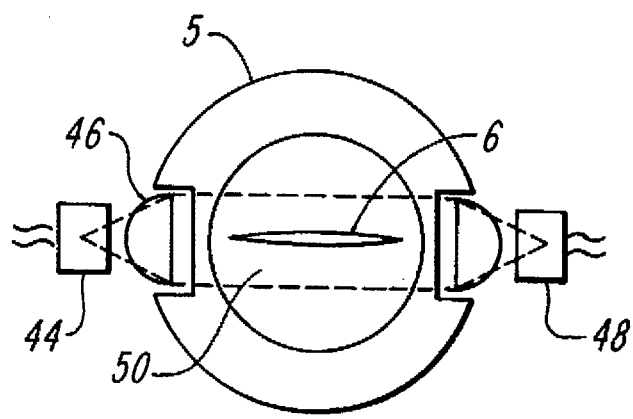
FIG. 4A shows a cross section of the pump lumen along line A-A' of a circulatory assist device at the end of systole.
Figure 4B:
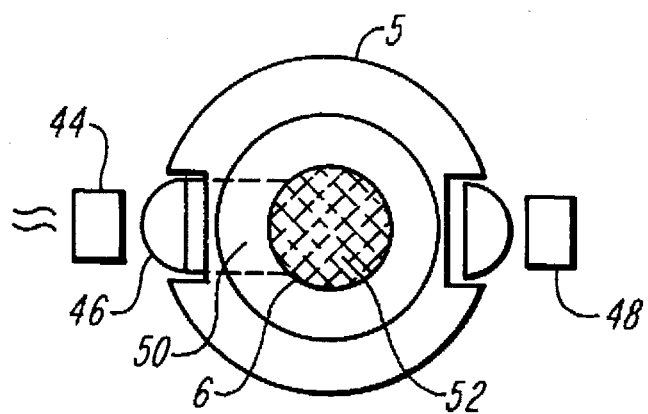
FIG. 4B shows a cross section of the pump lumen along line A-A' of a circulatory assist device at the end of diastole.

The embodiment illustrated in FIG. 3 advantageously allows the single pneumatic drive 21 to control the action of both chambers 12 and 14. In particular, pneumatic drive 21 directly supplies a variable pressure through line 32 to chamber 12, thus controlling the pumping action along segment 11. Pneumatic drive 21 simultaneously supplies flow restrictor 23 with a variable pressure through pneumatic lines 32 and 34. The output of flow restrictor 23, coupled to chamber 14, controls the pumping along segment 14. As a result, the single pneumatic drive 21 controls the restriction and dilation of both chambers 12 and 14. This approach, that utilizes a common pneumatic driver, reduces the complexity of circulatory assist device 5 and improves the overall reliability of assist device 5. Additionally this embodiment includes a monitor 3, formed as shown in FIGS. 4A and 4B, which senses the filling of lumen A and provides a triggering signal to drive 21.

Pneumatic drive 21 can be either include a compressor/vacuum pump with one plenum at high pressure and the other plenum at low pressure, or a piston driven pump. Flow restrictor 23 can be a clamp, diaphragm, valve, or other means for selectively restricting or slowing the flow through pneumatic line 36. Flow restrictor 23 allows the pumping action of chambers 12 and 14 to be controlled by one pneumatic drive. For example, the pneumatic drive can initiate a systolic action by changing the pressure from low to high pressure. This change in pressure is rapidly initiated by inflow chamber 12, causing a restriction of segment 11. The change in pressure in pump chamber 14, however, is slowly initiated because of flow restrictor 23. Thus, flow restrictor 23 delays in time the pumping and filling action of pump chamber 14 with respect to inflow chamber 12.

FIG. 3 also shows an embodiment of the invention wherein tube 4 has molded or shaped sections. For example, segments 11, 13 and 15 can be partially flattened using shaped internal molds and external clamps during the manufacture of circulatory apparatus 5. The shapes formed by the various molds and clamps can then be heat formed, giving tube 4 a new memory shape.

This technique of forming memory shapes in tube 4 can be used to create valve-like structures along the tube, particularly at segments 11 and 15, and to create a narrowed tubular section at segment 13 that aids in pumping. Preferably, the valve-like structures at segments 11 and 15 are formed in the closed position as the memory shape. For example, in a circulatory assist apparatus capable of moving up to 0.5 liters per minute, segments 11 and 15 form an approximately 2 cm long shape that transitions from a circular cross section to a narrow line contact region and back to a circular cross section. While segment 13, in comparison, is heat formed in a position approximately halfway between its fully dilated and fully restricted positions. In addition, segment 13 can be tapered to insure that circulatory device 5 ejects material from the direction of inlet 8 towards the direction of outlet 10.

FIGS. 4A and 4B both illustrate a cross section of circulatory assist device 5 having a system for monitoring the filling and emptying of lumen 6. The monitoring system comprises light emitting diode 44 (hereinafter "LED"), lens 46, photodiode 48, and radiation path 50 produced by LED 44. FIG. 4A illustrates device 5 at the end of systole, while FIG. 4B illustrates device 5 at the end of diastole.

LED 44 and receiver 48 are mounted on opposite sides of lumen 6 with their optical axis parallel to the flattened walls of tureen 6 while empty. As shown in FIG. 4A, this part of the cycle yields the maximum radiation intensity signal on receiver 48. As lumen 6 fills, the shape of the lumen reverts to a cylinder and the circulating fluid or gas 52 absorbs emitted radiation 50 from LED 44, leading to reduced signal intensity detected by receiver 48.

The algorithm for controlling the beat rate of circulatory assist device 5 makes its decision based on the degree to which lumen 6 is filled at the end of diastole. If the lumen is full, indicating that the diastolic duration may be longer than is necessary, the beat rate would be increased for the next beat. However, if the lumen is only partially full, the beat rate would be decreased, thus allowing for a longer diastolic duration for filling. Thus faster filling as a result of higher environmental pressure will result in increased beat rate and vice versa.

The monitoring system disclosed herein advantageously allows circulatory assist device 5 to respond to changes in the rate of flow. The monitoring device 3 disclosed herein monitors and communicates to circulatory assist device 5 any change in flow rate in the pathway external to device 5. The circulatory assist device 5 then adjusts its rate of pumping in response to the new rate of flow.

The invention being thus disclosed and described in connection with the illustrated embodiments, variations and modifications thereof will occur to those skilled in the art, and are intended to be included within the scope of the invention, as defined by the claims appended hereto.

What is claimed is:

1. A circulatory support apparatus for insertion into a pathway to provide pulsatile fluid flow through said pathway, comprising:

a tube formed of a flexible and restrictable material elongated along a first axis, said tube having an inlet for coupling to said pathway, an outlet for coupling to said pathway, an outer circumferential surface, a lumen within said tube connecting the inlet and the outlet and extending beyond said outlet at one end to form a lumen extension, said tube having first, second, and third segments, first restricting means for selectively restricting the diameter of said lumen in said first segment of said tube distal the inlet, second restricting means for restricting the diameter of said lumen in said second segment of said tube proximal the outlet, third restricting means for selectively restricting the diameter of said lumen in said third segment of said tube positioned between said first and said second restricting means, a first controller coupled with said first restricting means and said third restricting means for sequentially controlling said first restricting means and said third restricting means, such that restriction of said lumen in said third segment is phase delayed with respect to restriction of said lumen in said first segment, and a second controller for passively controlling the restriction of said second restricting means to maintain flow through said second restricting means within a predetermined range.

2. A circulatory support apparatus according to claim 1, wherein:

said second controller comprises an outflow chamber surrounding a longitudinal section along said first axis of the outer circumferential surface of said tube, said second restricting means controlling the fluid flow in said outflow chamber to limit the pressure in said lumen extension.

3. A circulatory support apparatus according to claim 2, further comprising:

a diaphragm mounted in contact with said lumen extension, a pressure conduit having a first end connected to said second restricting means and a second end sealed with said diaphragm, wherein said diaphragm communicates pressure-wise with said lumen extension to control said second restricting means in accordance with pressure in said lumen extension to keep said lumen extension pressure within said predetermined range, and wherein said second segment is normally closed.

4. A circulatory support apparatus according to claim 1, wherein:

said first segment lumen is flattened to normally restrict the inlet, said second segment lumen is flattened to normally restrict the outlet, and said third segment lumen is flattened to normally restrict the lumen approximately halfway between a fully open and a fully closed position.

5. A circulatory support apparatus according to claim 4, further comprising:

a detector mounted adjacent the lumen for monitoring the filling of the lumen and for generating a signal indicative of the degree of fill of said lumen, said signal being coupled to said first controller, said first controller controlling the time sequence of operation of said first and third restricting means in accordance with said signal.

6. A circulatory support apparatus according to claim 5, wherein:

said detector comprises a light emitting diode and receiver mounted on opposite sides of said third segment and having an optical axis intersecting with said flattened third segment lumen.

7. A circulatory support apparatus according to claim 1, wherein:

said first restricting means comprises an inflow chamber for surrounding a longitudinal section along said first axis of the outer circumferential surface of said restrictable tube, and for pressurizing said inflow chamber at a first variable pressure, and said third restricting means comprises a pump chamber for surrounding a longitudinal section along said first axis of the outer circumferential surface of said tube, and for pressurizing said pump chamber at a second variable pressure.

8. A circulatory support apparatus according to claim 7, wherein said first controller further comprises:

a pneumatic drive for generating a cyclical variable pressure level, and an adjustable flow restrictor for adjusting the phase difference between a change in said first variable pressure and a change in said second variable pressure.

9. A circulatory support apparatus according to claim 1 wherein said restrictable tube is formed of polyetherurethane.

* * * * *